United States Patent
Limsopatham et al.

(10) Patent No.: US 12,159,722 B2
(45) Date of Patent: Dec. 3, 2024

(54) LEVERAGING DEEP CONTEXTUAL REPRESENTATION, MEDICAL CONCEPT REPRESENTATION AND TERM-OCCURRENCE STATISTICS IN PRECISION MEDICINE TO RANK CLINICAL STUDIES RELEVANT TO A PATIENT

(71) Applicant: Microsoft Technology Licensing, LLC, Redmond, WA (US)

(72) Inventors: Nut Limsopatham, Seattle, WA (US); Liang Du, Redmond, WA (US); Robin Abraham, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 878 days.

(21) Appl. No.: 17/102,292

(22) Filed: Nov. 23, 2020

(65) Prior Publication Data
US 2022/0165430 A1  May 26, 2022

(51) Int. Cl.
*G16H 50/70* (2018.01)
*G06F 40/30* (2020.01)
*G06N 3/08* (2023.01)
*G16H 10/60* (2018.01)
*G16H 50/50* (2018.01)

(52) U.S. Cl.
CPC ............. *G16H 50/70* (2018.01); *G06F 40/30* (2020.01); *G06N 3/08* (2013.01); *G16H 10/60* (2018.01); *G16H 50/50* (2018.01)

(58) Field of Classification Search
CPC ........ G16H 50/70; G16H 50/50; G16H 10/60; G06F 40/30; G06N 3/08
USPC ......................................................... 703/21
See application file for complete search history.

(56) References Cited

U.S. PATENT DOCUMENTS

2013/0332187 A1* 12/2013 Maman .................. G16H 50/20
705/2

OTHER PUBLICATIONS

Rybinski_2020 (Clinical trial research: using biomedical language understanding models for re-ranking, Aug. 18, 2020). (Year: 2020).*

(Continued)

*Primary Examiner* — Brian S Cook
(74) *Attorney, Agent, or Firm* — RAY QUINNEY & NEBEKER P.C.; Adam K. Richards

(57) ABSTRACT

A relevance system ranks a set of medical studies based on a relevance of each medical study in the set of medical studies to a patient profile. The relevance system includes a relevance model. The relevance model determines a relevance of each medical study to the patient profile based on a semantic relationship score, a concept relationship score, and a term-occurrence score. The semantic relationship score is a measure of a similarity in semantic meaning of a medical study and a patient profile. The concept relationship score is a measure of the closeness of medical concepts in a medical study to medical concepts in a patient profile. The term-occurrence score is a measure of occurrences of terms in a medical study that also appear in a patient profile and the statistical significances of the terms.

20 Claims, 8 Drawing Sheets

(56) References Cited

OTHER PUBLICATIONS

Elsken, et al., "Neural Architecture Search: A Survey", In Repository of arXiv:1808.05377v1, Aug. 16, 2018, pp. 1-16.
Han, et al. "Learning-to-Rank with BERT in TF-Ranking", In Repository of arXiv:2004.08476v3, Jun. 8, 2020, pp. 1-6.
Li, Hang, "A Short Introduction to Learning to Rank", In Journal of IEICE Transactions on Information and Systems vol. 94, Issue 10, Oct. 1, 2011, pp. 1854-1862.

* cited by examiner

LEVERAGING DEEP CONTEXTUAL REPRESENTATION, MEDICAL CONCEPT REPRESENTATION AND TERM-OCCURRENCE STATISTICS IN PRECISION MEDICINE TO RANK CLINICAL STUDIES RELEVANT TO A PATIENT

CROSS-REFERENCE TO RELATED APPLICATIONS

N/A

BACKGROUND

Precision medicine may be a medical model that customizes healthcare (such as medical decisions, treatments, practices, and products) to a particular patient or group of patients based on the characteristics of the particular patient or the group of patients and on characteristics of the disease afflicting the particular patient or the group of patients. The goal of precision medicine may be to protect a patient's health by measuring factors (such as genes, behaviors, environment, and disease characteristics) and tailoring treatments based on those measurements rather than using the same approach for everyone. Precision medicine may look to medical data, including relevant medical studies, to identify treatments for a particular patient.

SUMMARY

In accordance with one aspect of the present disclosure, a system is disclosed for determining a relevance of an input medical study to an input patient profile. The system includes one or more processors, memory in electronic communication with the one or more processors, and instructions stored in the memory. The instructions are executable by the one or more processors to determine a term-occurrence score for the input medical study and the input patient profile. The term-occurrence score is based on a presence in the input medical study of one or more terms that appear in the input patient profile and statistical weights associated with the one or more terms. The instructions are also executable by the one or more processors to identify a first set of medical concepts contained in the input medical study and a second set of medical concepts contained in the input patient profile. The instructions are also executable by the one or more processors to determine a concept relationship score for the first set of medical concepts and the second set of medical concepts. The concept relationship score measures a closeness of relationship between the first set of medical concepts and the second set of medical concepts. The instructions are also executable by the one or more processors to determine a semantic relationship score for the input medical study and the input patient profile based on a semantic meaning of text contained in the input medical study and the input patient profile. The instructions are also executable by the one or more processors to determine a probability that the input medical study is relevant to the input patient profile based on the term-occurrence score, the concept relationship score, and the semantic relationship score.

Determining the semantic relationship score for the input medical study and the input patient profile may be further based on the first set of medical concepts and the second set of medical concepts.

The system may further include determining the semantic meaning of text contained in the input medical study and the input patient profile based on deep contextual representation.

Determining the semantic meaning of text contained in the input medical study and the input patient profile based on deep contextual representation may be based on a BERT (bidirectional encoder representations from transformers) model or an ELMo (embeddings from language models) model.

The statistical weights associated with the one or more terms may be based on a statistical analysis of a corpus of medical studies.

Determining the term-occurrence score may be further based on a number of appearances of the one or more terms in the input medical study.

Determining the concept relationship score for the first set of medical concepts and the second set of medical concepts may be based on a knowledge graph of medical concepts. The knowledge graph may include links among the medical concepts and the knowledge graph may include the first set of medical concepts and the second set of medical concepts.

Medical concepts in the first set of medical concepts and the second set of medical concepts may be contained in a Unified Medical Language System (UMLS).

The system may further include ranking the input medical study against one or more other medical studies based on the probability that the input medical study is relevant to the input patient profile and probabilities that the one or more other medical studies are relevant to the input patient profile.

The system may further include selecting the one or more other medical studies from a set of medical studies based on term-occurrence scores for each medical study in the set of medical studies and the input patient profile.

In accordance with another aspect of the present disclosure, a method is disclosed for determining semantic similarity between an input medical study and an input patient profile. The method includes receiving the input medical study and the input patient profile, identifying a first set of medical concepts in the input medical study, identifying a second set of medical concepts in the input patient profile, determining a first semantic meaning of text in the input patient profile, and determining a second semantic meaning of text in the input medical study. The method also includes determining a semantic similarity score for the input patient profile and the input medical study based on the first set of medical concepts, the second set of medical concepts, the first semantic meaning, and the second semantic meaning.

Determining the first semantic meaning and the second semantic meaning may be based on deep contextual representation.

Determining the first semantic meaning and the second semantic meaning may be based on deep contextual representation is based on a BERT model or an ELMo model.

In accordance with another aspect of the present disclosure, a computer-readable medium is disclosed. The computer-readable medium includes instructions that are executable by one or more processors to cause a computing system to receive a medical study and a patient profile and determine a term-occurrence score for the medical study and the patient profile. The term-occurrence score is based on a presence in the medical study of one or more terms that appear in the patient profile and statistical weights associated with the one or more terms. The instructions are also executable by one or more processors to cause a computing system to identify a first set of medical concepts contained in the medical study and a second set of medical concepts contained in the patient profile. The instructions are also executable by one or more processors to cause a computing system to determine a concept relationship score for the first set of medical concepts and the second set of medical concepts. The concept relationship score measures a closeness of relationship between the first set of medical concepts and the second set of medical concepts. The instructions are also executable by one or more processors to cause a computing system to determine a semantic relationship score for the medical study and the patient profile based on a semantic meaning of text contained in the medical study and the patient profile and based on the first set of medical concepts and the second set of medical concepts. The instructions are also executable by one or more processors to cause a computing system to determine a probability that the medical study is relevant to the patient profile based on the term-occurrence score, the concept relationship score, and the semantic relationship score.

The statistical weights associated with the one or more terms may be based on a statistical analysis of a corpus of medical studies.

Determining the term-occurrence score may be further based on a number of appearances of the one or more terms in the medical study.

Determining the concept relationship score for the first set of medical concepts and the second set of medical concepts may be based on a knowledge graph of medical concepts. The knowledge graph may include links among the medical concepts and the knowledge graph comprises the first set of medical concepts and the second set of medical concepts.

Medical concepts in the first set of medical concepts and the second set of medical concepts may be contained in a Unified Medical Language System (UMLS).

The computer-readable medium may further include instructions that are executable by the one or more processors to cause the computing system to rank the medical study against one or more other medical studies based on the probability that the input medical study is relevant to the patient profile and probabilities that the one or more other medical studies are relevant to the input patient profile.

The computer-readable medium may further include instructions that are executable by the one or more processors to cause the computing system to select the one or more other medical studies from a set of medical studies based on term-occurrence scores for each medical study in the set of medical studies and the input patient profile.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description that follows. Features and advantages of the disclosure may be realized and obtained by means of the systems and methods that are particularly pointed out in the appended claims. Features of the present disclosure will become more fully apparent from the following description and appended claims, or may be learned by the practice of the disclosed subject matter as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. Understanding that the drawings depict some example embodiments, the embodiments will be described and explained with additional specificity and detail through the use of the accompanying drawings in which.

DETAILED DESCRIPTION

Figure 1:
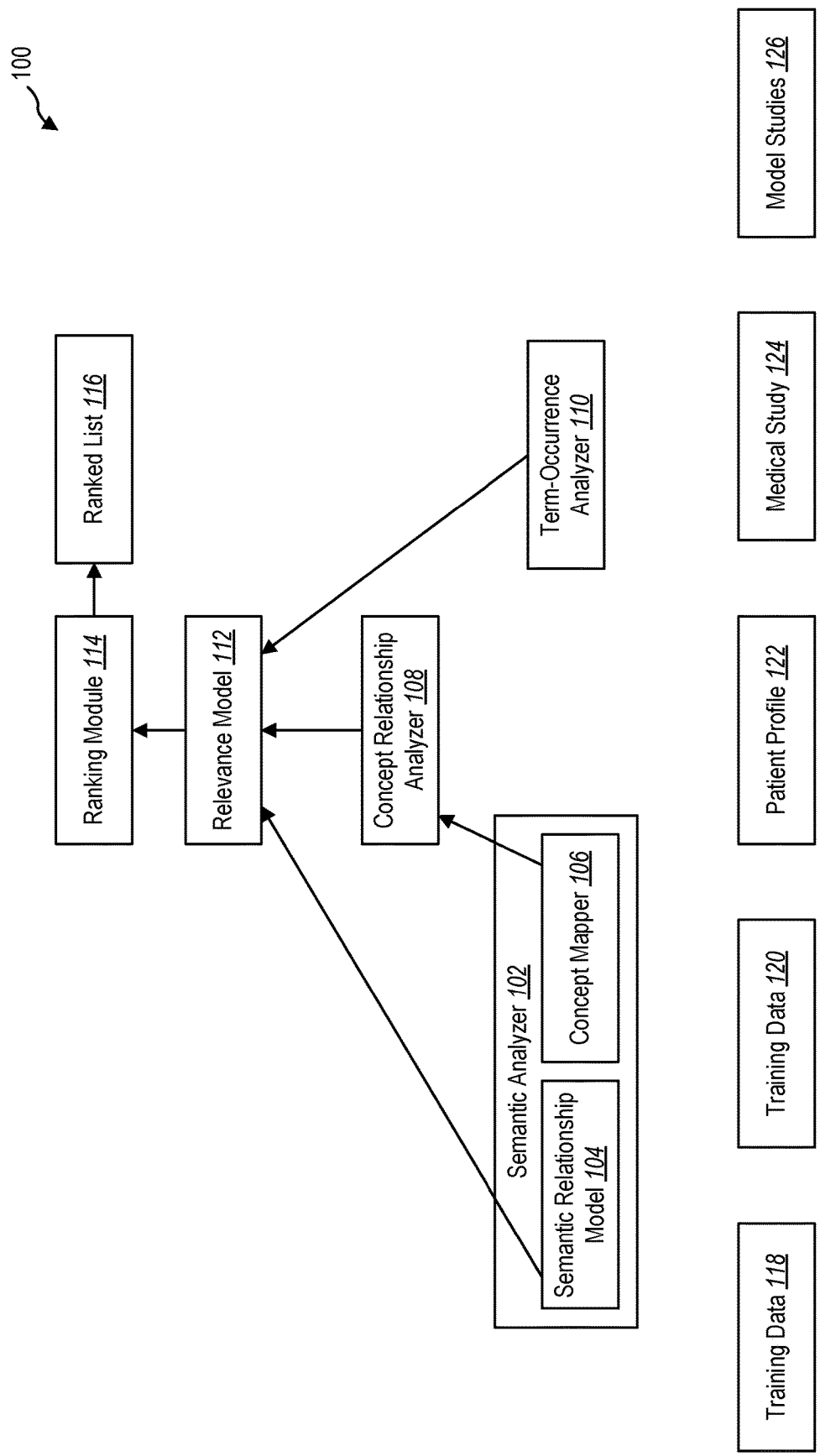
FIG. 1 illustrates an example system for ranking a set of medical studies based on predicated relevance to a patient profile.

Precision medicine may involve using treatments that are personalized to individual patients. The treatments may be based on a particular patient's genetics, environment, and lifestyle choices. More broadly, precision medicine may be a medical model that customizes healthcare (such as medical decisions, treatments, practices, and products) to a particular patient or group of patients based on the characteristics, environment, and lifestyle choices of the particular patient or the group of patients and on characteristics of the disease afflicting the particular patient or the group of patients. Patients may be grouped by biomarkers, clinical features, demographics (e.g., age, race, sex), disease subtypes, family history, genomics, health history, lifestyle (e.g., alcohol, exercise, nutrition, smoking, weight), molecular subpopulations, preferences, risk profiles, and socioeconomics.

The goal of precision medicine may be to protect a patient's health by measuring factors (such as genes, behaviors, environment, and disease characteristics) and tailoring treatments based on those measurements rather than using the same approach for everyone. Precision medicine may include classifying individuals into subpopulations that differ in their susceptibility to a particular disease, in the biology or prognosis of those diseases they may develop, or in their response to specific treatment. Precision medicine may involve analyzing a patient's disease at the molecular level or performing genomic tests on a patient.

Precision medicine may allow doctors and researchers to predict more accurately which treatment and prevention strategies for a particular disease will work in which groups of people. Precision medicine may be in contrast to a one-size-fits-all approach in which disease treatment and prevention strategies may be developed for the average person with less consideration for the differences between individuals.

Implementing precision medicine in practice may be challenging. Determining a treatment tailored to a particular patient may involve analyzing known medical studies and real-world data to identify medical studies and treatments that fit the particular patient's genetics, environment, lifestyle choices, and symptoms. A large corpus of potentially relevant medical studies may exist. And data aggregators may collect and aggregate large amounts of patient and treatment data. Tremendous effort may be required to comb through existing clinical research studies to identify the studies that are relevant to a particular patient.

The present disclosure describes systems and methods for efficiently and effectively ranking medical studies (which may include clinical studies and trial notes) based on their relevance to a particular patient. The relevance of a medical study to a particular patient may be a measure of the likelihood that the medical study describes a treatment option that is likely to be effective for the particular patient. The relevance of a medical study to a particular patient may be a measure of the likelihood that the medical study describes a treatment option that is tailored to a condition of the particular patient. A relevance system may leverage semantic analysis (such as deep contextual representation), medical concept representation, and term-occurrence statistics to overcome the unique challenges in searching voluminous amounts of clinical studies that contain a significant amount of complex terminology, synonyms, and negation. The relevance system may learn, through a deep neural network architecture, to use term-occurrence statistics, medical concept representation, and deep contextual representation to predict a probability that a medical study is relevant to a patient. The relevance system may rank medical studies based on these predicted probabilities. Once the medical studies are ranked, a medical professional may more easily identify medical and clinical studies that will assist the medical professional in determining a medical treatment tailored to the particular patient.

The relevance system may include a relevance model. The relevance model may be a supervised learning model trained to output a probability that a medical study is relevant to a patient profile. The relevance model may be trained on labeled training data. The labeled training data may include sets of example input signals (of the type described below). Each set of example input signals may be associated with an example medical study and an example patient profile. Each set of example input signals may have an associated label. The associated label may be a relevance score of the example medical study to the example patient profile. The relevance score may be "1" for relevant and "0" for not relevant.

After training, the relevance model may receive a particular medical study, a particular patient profile, and three input signals and output a probability that the particular medical study is relevant to the particular patient profile based on the three input signals.

A first input signal may be a relationship score for the particular patient profile and the particular medical study. The relationship score may be a measure of the similarity of the semantic meaning of text contained in the particular patient profile and the semantic meaning of text contained in the particular medical study. The relationship score may be based on deep contextual representation. The relationship score may be based in part on medical concepts contained in the particular patient profile and the particular medical study.

A second input signal may be a concept relationship score. The concept relationship score may be a measure of how closely related medical concepts contained in the particular medical study are to medical concepts contained in the particular patient profile. The relationship system may determine the medical concepts contained in the particular medical study and the particular patient profile.

A third input signal may be a term-occurrence score for the particular medical study and the particular patient profile. The term-occurrence score may be based on occurrences of terms in the particular patient profile that also appear in the particular medical study (overlapping terms). The term-occurrence score may be based on the number of occurrences of the overlapping terms in the particular medical study and the statistical significance of the overlapping terms. The statistical significance of the overlapping terms may be based on a statistical analysis of a corpus of medical studies.

A semantic relationship model may output the first signal. The semantic relationship model may be a supervised learning model trained to output a relationship score for two sets of texts (such as a patient profile and a medical study). The training data may be a set of labeled examples. The examples may be example pairs of medical studies and patient profiles. The label for each example pair may be a relationship score (such as a number between 0 (not related) and 1 (highly related)). Once trained, the semantic relationship model may receive a patient profile and a medical study and provide a relationship score for the patient profile and the medical study. The relationship score may represent a semantic similarity of the patient profile and the medical study. In determining the relationship score, the semantic relationship model may consider the medical concepts contained in the patient profile and the medical study. The relationship score may be higher when the semantic meaning of text in the patient profile is similar to the semantic meaning of text in the medical study than when the semantic meaning of text in the patient profile is different from the semantic meaning of text in the medical study.

A concept relationship analyzer may output the second signal. The concept relationship analyzer may output a concept relationship score. The concept relationship score may be a measure of how closely related medical concepts contained in a patient profile are to medical concepts contained in a medical study. The concept relationship score may be higher when the medical concepts contained in the patient profile are identical to or closely related to the medical concepts contained in the medical study than when the medical concepts contained in the patient profile are not related to the medical concepts contained in the medical study. Some examples of when a first medical concept may be closely related to a second medical concept may be when the first medical concept is a condition similar to the second medical concept, when the first medical concept causes or is caused by the second medical concept, or when the first medical concept and the second medical concept are frequently treated in the same way. The concept relationship score may be a similarity score or a probability of similarity. The concept relationship analyzer may use a database that describes relationships among medical concepts to calculate the concept relationship score. The concept relationship analyzer may score a relationship between two medical concepts based on a type of relationship of the two medical concepts described in the database. The database may include a knowledge graph that links medical concepts.

A term-occurrence analyzer may output the third signal. The term-occurrence analyzer may determine a term-occurrence score for two texts (such as a patient profile and a medical study). Before providing the term-occurrence score, the term-occurrence analyzer may analyze a large corpus of documents (such as a large corpus of medical studies). The term-occurrence analyzer may perform a statistical analysis on the large corpus of documents to determine a statistical significance of terms contained in the large corpus of documents. The term-occurrence analyzer may use a pre-determined function and the statistical significance of terms contained in the large corpus of documents to determine the term-occurrence score for the two texts. The term-occurrence score may be based on the number of occurrences in the medical study of terms contained in the patient profile and the statistical significance of those terms. The term-occurrence similarity score may be higher when the medical study contains a large number of statistically significance terms that are contained in the patient profile than when the medical study contains a small number of statistically significant terms that are contained in the patient profile.

The relevance system may combine benefits of term-occurrence statistics (ranking documents based on the occurrences of important terms), medical concept representation (representing medical terms in a conceptual unit to lessen the ambiguity and misrepresentation of medical terms), and deep contextual representation (measuring similarity between clinical studies and patient profiles based on the semantic information learned from large-scale corpora). Due to its end-to-end fashion, the relevance system learns to recognize medical concepts and learns how each concept contributes to the relevance of a medical document to a patient profile. As a result, the relevance system learns to ignore medical documents that contain low-impact medical concepts but identify medical documents that include high-impact medical concepts. Furthermore, by optimizing together term-occurrence statistics, medical concept knowledge, and semantic information, the relevance system learns to measure relevance based on term-occurrence and semantic information effectively. As a result, the relevance system can select relevant documents that do not contain any query terms (i.e., terms in a patient profile) and avoid retrieving non-relevant documents that might contain some query terms. Moreover, the relevance system can adjust to leverage potential medical concepts when ranking medical documents even though the lexicon related to the concepts may not be obvious or detected by a medical concept recognition system.

The relevance system has applications beyond identifying medical studies that are relevant to a particular patient. The relevance system may enable ranking and identifying patients for a particular study. A single study may be compared against a database of patient profiles to rank and identify patients who are a good fit for the single study. The relevance system may enable ranking and identifying experts (such as doctors) for a study. A single study may be compared against a database of experts to rank and identify experts with expertise on the subject matter of the single study. The experts may be represented in the database by records of their patients. The relevance system may enable ranking and identifying similar studies. A set of criteria may be compared against a database of studies to identify similar studies.

Although the relevance system is described above in the context of patients and medical studies, the relevance system is not limited to the medical context. The relevance model may be applied in other contexts to predict a relevance of a first text to a second text. For example, the relevance system may be applied in the field of academic research to identify publications and research papers that are relevant to another paper or topic. As another example, the relevance system may be applied to identify court decisions relevant to a legal dispute.

FIG. 1 illustrates an example system 100 for predicting relevance of a clinical study to a particular patient profile. The system 100 may include a semantic analyzer 102, a concept relationship analyzer 108, a term-occurrence analyzer 110, a relevance model 112, and a ranking module 114.

The semantic analyzer 102 may perform natural language processing and semantic analysis on two or more texts. Semantic analysis may include analysis that goes beyond cataloging words contained in a text. Semantic analysis may include analysis intended to derive meaning from natural language (such as a collection of words). Semantic analysis may involve interpreting words, phrases, clauses, sentences, paragraphs, or documents. Semantic analysis may include analyzing grammatical structure and identifying relationships between words. Semantic analysis may include word-sense disambiguation and relationship extraction.

The two or more texts may include a patient profile 122 and a medical study 124. The patient profile 122 may include text regarding a particular patient. The patient profile 122 may include text regarding the particular patient's symptoms, past and current treatments, genetics, environmental conditions, lifestyle choices, family history, and medical history. The patient profile 122 may include text regarding the particular patient's biomarkers, clinical features, demographics (e.g., age, race, sex), disease subtypes, genomics, health history, lifestyle (e.g., alcohol, exercise, nutrition, smoking, weight), molecular subpopulation, preferences, risk profiles, and socioeconomics. The medical study 124 may include text regarding a clinical study, a medical study, a clinical note, or treatment of a patient. The medical study 124 may include information regarding participants in the clinical study, the medical study, the clinical note, or the treatment (including the types of information included in the patient profile 122), specific interventions or treatments used in the medical study, the clinical study, the clinical note, or the treatment, and outcomes of the medical study, the clinical study, the clinical note, or the treatment.

The semantic analyzer 102 may include a semantic relationship model 104 and a concept mapper 106.

The semantic relationship model 104 may be a supervised learning model that measures a relationship (such as a similarity) between a first set of words and a second set of words. The first set of words may be the patient profile 122. The second set of words may be the medical study 124. The semantic relationship model 104 may receive the first set of words and the second set of words and output a relationship score based on comparing the first set of words and the second set of words. The relationship score may be a measure of how similar the first set of words is to the second set of words. The relationship score may be a measure of closeness or similarity between a meaning of the first set of words and a meaning of the second set of words. The relationship score may be a measure of closeness or similarity between a semantic meaning of the first set of words and a semantic meaning of the second set of words. The relationship score may be based in part on concepts (such as medical concepts) contained in the first set of words and the second set of words.

Comparing the first set of words and the second set of words may include performing semantic analysis on the first set of words and the second set of words. Comparing the first set of words and the second set of words may include comparing a semantic meaning of the first set of words with a semantic meaning of the second set of words. The semantic relationship model 104 may utilize deep contextual representation to determine a semantic meaning of the first set of words and a semantic meaning of the second set of words and to measure the relationship between the first set of words and the second set of words. Deep contextual representation may represent a word as a function of the entire input text, taking word dependencies and sentence structures into consideration.

The semantic relationship model 104 may utilize one or more deep contextual representation models to perform semantic analysis. The deep contextual representation models may be pre-trained neural language models such as ULMFiT (universal language model fine-tuning), ELMo (embeddings from language models), or BERT (bidirectional encoder representations from transformers). These models may be trained in two steps. The models may be first trained on large amounts of text using semi-supervised learning. In this way, the contextual representations encode general language patterns. The models may then be trained on labeled examples to perform a specific task.

The semantic relationship model 104 may be trained using one or more sets of training data. The one or more sets of training data may include training data 118. The training data 118 may include a set of labeled examples. Each example may include a first text and a second text. The first text may be a patient profile and the second text may be a medical study. The label for each example may be a relationship score. The relationship score may be a measure of a relationship between the first text and the second text. The relationship score may be a measure of similarity, such as semantic similarity, between the first text and the second text. The relationship score may be a measure of the relevance of the second text to the first text. In some designs, the relationship score may be a zero (no relationship exists) or a one (a relationship exists).

Constructing the semantic relationship model 104 may involve training the semantic relationship model 104 on a set of example pairs of patient profiles and medical studies that have associated relationship labels. During training, the semantic relationship model 104 may also receive information about medical concepts contained in the example pairs of patient profiles and medical studies. Once trained, the semantic relationship model 104 may receive a patient profile (such as the patient profile 122) and a medical study (such as the medical study 124) and provide a relationship score for the patient profile and the medical study. In determining the relationship score, the semantic relationship model 104 may consider medical concepts contained in the patient profile and the medical study. Training the semantic relationship model 104 may allow the semantic relationship model 104 to make accurate predictions about whether a medical study is semantically similar to a patient profile.

The concept mapper 106 may be a machine learning model that maps text in a first set of words to a concept. The concept may be included in a set of discrete concepts. Mapping the text to the concept may include identifying the text in the first set of words that maps to the concept. The concept may be a medical concept and the set of discrete concepts may be a set of discrete medical concepts. The set of discrete medical concepts may be medical concepts contained in the Unified Medical Language System (UMLS). The concept mapper 106 may map different sets of text to a same medical concept. For example, the concept mapper 106 may map all the following sets of words to a medical concept of "headache": "headache," "cranial pain," and "cephalgia head pain."

The concept mapper 106 may be trained on training data 120 to map text to a concept. The training data 120 may be a set of labeled examples. Each example may include text. The label for each example may be a concept. Thus, constructing the concept mapper 106 may involve training the concept mapper 106 on a set of texts with associated concept labels. Once trained, the concept mapper 106 may receive a patient profile or a medical study and output one or more concepts contained in the patient profile or the medical study. The one or more concepts may represent medical terms in a conceptual unit to lessen the ambiguity and misrepresentation of medical terms.

The concept relationship analyzer 108 may measure a relationship between two sets of concepts. Each of the two sets of concepts may contain one or more medical concepts. For example, a first set of concepts may be medical concepts contained in a patient profile, and a second set of concepts may be medical concepts contained in a medical study. The concept relationship analyzer 108 may use a database to measure the relationship between the two sets of concepts. The database may describe relationships between concepts and link related concepts. The concept relationship analyzer 108 may receive the two sets of concepts from the concept mapper 106. The concept relationship analyzer 108 may include a function that scores the relationship between the two sets of concepts based on information in the database. The score may measure a closeness of the relationship between concepts contained in a first set of concepts and concepts contained in a second set of concepts.

The term-occurrence analyzer 110 may output a term-occurrence score for a first set of words and a second set of words. The term-occurrence score may be based on occurrences of terms in the second set of words that appear in the first set of words and a statistical significance of the terms. The term-occurrence analyzer 110 may use term-occurrence statistics to determine the term-occurrence score. Term-occurrence statistics may involve ranking documents based on the occurrences in the second set of words of important terms that appear in the first set of words. In term occurrence statistics, documents matching on high informative terms may receive a higher score than documents matching on low informative terms. It may be that terms that do not appear frequently are more informative because those terms distinguish a document from other documents. Term-occurrence statistics may include performing a statistical analysis of a large database of documents. The large database of documents may be a large database of medical studies and/or patient profiles. For example, the large database of documents may be medical studies 126. The medical studies 126 may include many medical studies like the medical study 124. The statistical analysis of the large database of medical studies and/or patient profiles may include determining statistical significances of terms that appear in the medical studies 126 based on the medical studies 126.

The term-occurrence analyzer 110 may include a function. The term-occurrence analyzer 110 may use the function to determine the term-occurrence score. The function may utilize the statistical significances of terms that the term-occurrence analyzer 110 determined through the statistical analysis of the large database of documents. The term-occurrence analyzer 110 may input the first set of words and the second set of words into the function to determine the term-occurrence score.

The relevance model 112 may be a machine learning model that determines a relevance score for a medical study and a patient profile. The relevance score may be a probability that the medical study is relevant to the patient profile. The medical study may be relevant to the patient profile when the medical study describes a treatment that may be effective for the patient profile or may be tailored to a condition of the patient profile. A first medical study with a higher relevance score for a patient profile than a second medical study for the patient profile may be more likely to contain effective treatment options for the patient profile than the second medical study.

The relevance model 112 may receive output from the semantic analyzer 102, the concept relationship analyzer 108, and the term-occurrence analyzer 110. The relevance model 112 may determine the probability that the medical study is relevant to the patient profile based on output received from the semantic analyzer 102, the concept relationship analyzer 108, and the term-occurrence analyzer 110. The output received from the semantic analyzer 102 may be a relationship score for the patient profile and the medical study. The output received from the concept relationship analyzer 108 may be a concept relationship score that measures a similarity between medical concepts contained in the patient profile and medical concepts contained in the medical study. The output received from the term-occurrence analyzer 110 may be a term-occurrence score for the medical study and the patient profile.

The relevance model 112 may be trained in order to predict the relevance of a medical study to a patient profile. The relevance model 112 may use labels from the training data 118 and outputs from the semantic analyzer 102, the concept relationship analyzer 108, and the term-occurrence analyzer 110 to learn to predict the relevance of a medical study to a patient profile. In the alternative, the relevance model 112 may be trained on example outputs and labels. In the alternative, the relevance model 112 may be trained using a combination of the two approaches. Once trained, the relevance model 112 may receive outputs from the semantic analyzer 102, the concept relationship analyzer 108, and the term-occurrence analyzer 110 that are based on a medical study and a patient profile and output a probability that the medical study is relevant to the patient profile.

The ranking module 114 may receive two or more medical studies and a relevance score for each of the two or more medical studies. The relevance scores may be the probabilities that each of the two or more medical studies is relevant to a patient profile. The ranking module 114 may rank the two or more medical studies based on the relevance scores. The ranking module 114 may output a ranked list 116. The ranked list 116 may order the two or more medical studies based on the relevance scores. For example, the ranked list 116 may order the two or more medical studies from highest relevance score to lowest relevance score.

Figure 2:
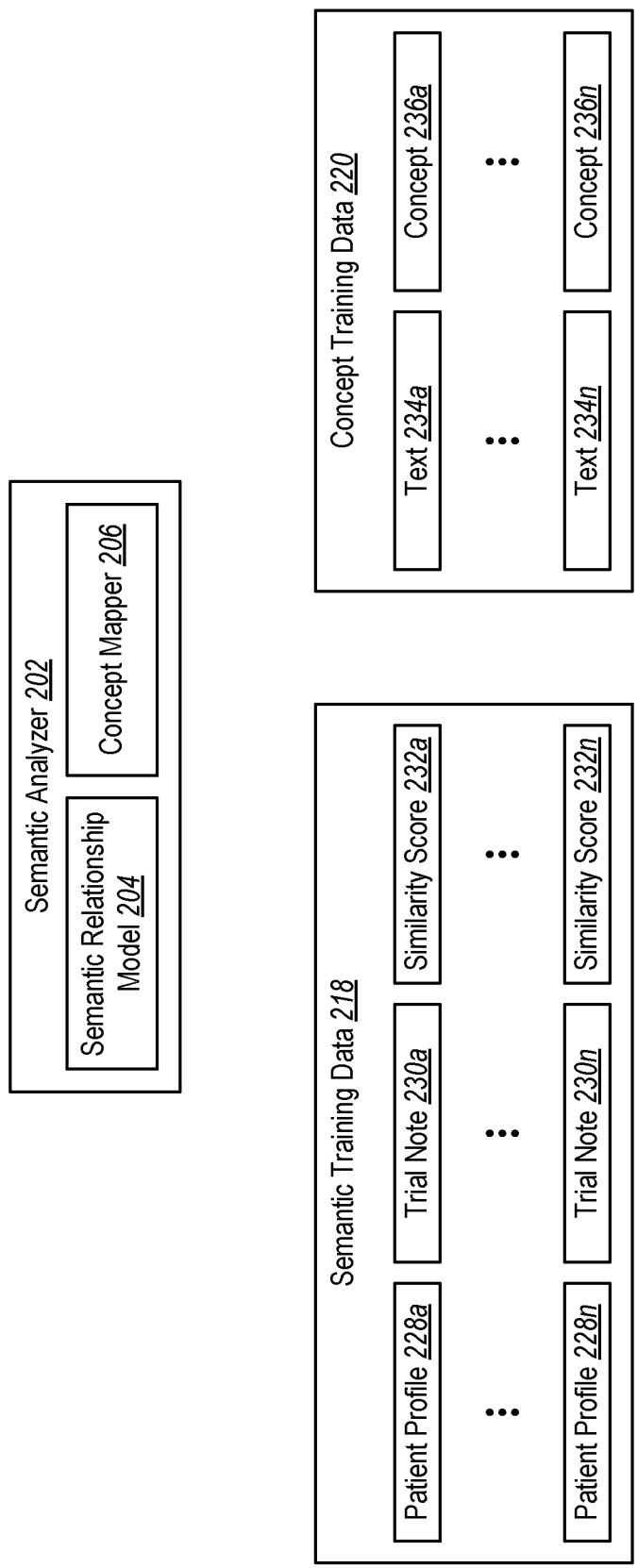
FIG. 2 illustrates an example semantic analyzer for determining a semantic similarity score for a patient profile and a medical study.

FIG. 2 illustrates an example semantic analyzer 202. The semantic analyzer 202 may include a semantic relationship model 204 and a concept mapper 206.

The semantic analyzer 202 may perform semantic analysis of two or more input texts. The two or more input texts may include a medical study (such as the medical study 124) and a patient profile (such as the patient profile 122).

The semantic relationship model 204 may output a semantic similarity score based on performing natural language processing and semantic analysis on two or more texts. The semantic similarity score may be a measure of distance (or closeness) between the two or more texts based on a likeness of their meaning or semantic content as opposed to lexicographical similarity. The semantic similarity score may indicate a similarity of the two or more texts at a semantic level, thus going beyond simple lexical matching methods. The semantic similarity score may estimate the strength of a semantic relationship between units of language, concepts, or instances contained in the two or more texts through a numerical description obtained according to a comparison of information supporting their meaning or describing their nature. The semantic relationship model 204 may determine the semantic similarity score based on deep contextual representation. The semantic similarity score may be based in part on medical concepts contained in the two or more texts, as determined by the concept mapper 206.

The semantic relationship model 204 may include a language representation model called BERT. BERT may stand for bidirectional encoder representations from transformers. BERT may be designed to pre-train deep bidirectional representations from unlabeled text by jointly conditioning on both left and right context in all layers. The pre-trained BERT model may be fine-tuned with just one additional output layer to create state-of-the-art models for a wide range of tasks, such as question answering and language inference, without substantial task-specific architecture modifications. BERT may alleviate unidirectionality constraint by using a "masked language model" (MLM) pre-training objective. The masked language model may randomly mask some of the tokens from the input, and the objective may be to predict the original vocabulary id of the masked word based only on its context. Unlike left-to-right language model pre-training, the MLM objective enables the representation to fuse the left and the right context, which allows for pre-training a deep bidirectional Transformer. In addition to the masked language model, BERT may use a "next sentence prediction" task that jointly pre-trains text-pair representations.

The semantic relationship model 204 may include a deep contextualized word representation model called ELMo (Embeddings from Language Models). An ELMo may be a deep contextualized word representation that models complex characteristics of word use (such as syntax and semantics) and how these uses vary across linguistic contexts. ELMo may model both (1) complex characteristics of word use (e.g., syntax and semantics) and (2) how these uses vary across linguistic contexts (i.e., to model polysemy). ELMo's word vectors may be learned functions of the internal states of a deep bidirectional language model (biLM), which may be pre-trained on a large text corpus. In other words, ELMo learns a linear combination of the vectors stacked above each input word for each end task. ELMo word representations may be functions of the entire input sentence. The ELMo word representations may be computed on top of two-layer biLMs with character convolutions, as a linear function of the internal network states. This setup may allow ELMo to do semi-supervised learning, where the biLM is pre-trained at a large scale and easily incorporated into a wide range of existing neural NLP architectures.

The semantic relationship model 204 may be trained on semantic training data 218. The semantic training data 218 may include patient profiles 228a-n, trial notes 230a-n, and similarity scores 232a-n. The semantic training data 218 may be organized in example sets. An example set may include a patient profile, a trial note, and a similarity score for the patient profile and the trial note. A trial note may be equivalent to a medical study (such as the medical study 124). The patient profile 228a, the trial note 230a, and the similarity score 232a may be an example set. The semantic relationship model 204 may learn to determine a semantic similarity score for a medical study and a patient profile by studying each example set in the semantic training data 218.

During the training process, the semantic relationship model 204 may also receive information from the concept mapper 206. In learning to determine a semantic similarity score for a medical study and a patient profile, the semantic relationship model 204 may consider the information received from the concept mapper 206. The information received from the concept mapper 206 may include medical concepts contained in a medical study and a patient profile. For example, the semantic relationship model 204 may receive, during a training phase, the patient profile 228a, the trial note 230a, and the similarity score 232a. The patient profile 228a and the trial note 230a may also be input into the concept mapper 206. The concept mapper 206 may output zero or more medical concepts contained in the patient profile 228a. The concept mapper 206 may output zero or more medical concepts contained in the trial note 230a. In learning to determine a similarity score for a medical study and a patient profile, the semantic relationship model 204 use the patient profile 228a, the trial note 230a, the similarity score 232a, the zero or more medical concepts contained in the patient profile 228a, and the zero or more medical concepts contained in the trial note 230a. In this way, the semantic relationship model 204 can learn to identify semantic similarity based in part on medical concepts contained in two texts.

The concept mapper 206 may map text in a patient profile or a trial note to a medical concept. The medical concept may be a medical concept contained in the Unified Medical Language System (UMLS). UMLS may include a comprehensive list of biomedical terms. UMLS may unify vocabularies used in different fields of biology and medicine. Medical concepts listed in multiple vocabularies may be brought together. UMLS may assign a unique identifier to each medical concept. A medical concept may be a meaning that can have many different names or different descriptions. A goal of the UMLS may be to understand the intended meaning of each name in each source vocabulary and to link all the names from all of the source vocabularies that mean the same thing. Thus, the concept mapper 206 may map non-identical groups of text to the same medical concept.

The concept mapper 206 may be trained on concept training data 220. The concept training data 220 may include texts 234a-n and concepts 236a-n. The concept training data 220 may be organized in example pairs. An example pair may include a text and a concept. For example, the text 234a and the concept 236a may be an example pair. The concept mapper 206 may learn to identify medical concepts in a medical study or a patient profile by studying each example pair in the concept training data 220.

Figure 3:
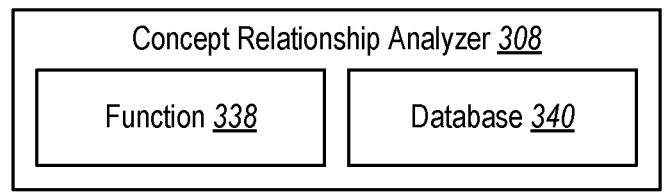
FIG. 3 illustrates an example concept relationship analyzer for determining a relationship score for two or more medical concepts.

FIG. 3 illustrates an example concept relationship analyzer 308. The concept relationship analyzer 308 may include a function 338 and a database 340.

The concept relationship analyzer 308 may output a concept relationship score for two sets of medical concepts. Medical concepts in the two sets of medical concepts may be contained in the UMLS. The concept relationship analyzer 308 may determine the concept relationship score based on a graph neural network. The concept relationship analyzer 308 may use the function 338 and the database 340 to determine the concept relationship score. The concept relationship score may be a measure of closeness a first set of concepts to a second set of concepts. The concept relationship score may be a measure of closeness of concepts in the first set of concepts to concepts in the second set of concepts. The concept relationship score may be based on a closeness of each concept in the first set of concepts to each concept in the second set of concepts. The closeness of two concepts may be based on information in the database 340. The first set of concepts may be medical concepts contained in a patient profile. The second set of concepts may be medical concepts contained in a trial note.

The function 338 may be a static, pre-determined function. The function 338 may receive two sets of medical concepts and output a concept relationship score. The two sets of medical concepts may include a first set of medical concepts in a patient profile and a second set of medical concepts in a medical study. The concept relationship analyzer 308 may extract information from the database 340 in determining the concept relationship score. One example function may be as follows:

$$= \sum_{i=0}^{q} \sum_{j=0}^{d} \text{MAX}(Sim(c_i, c_j))$$

The $Sim(c_i, c_j)$ may be a function that outputs a similarity score for a first medical concept $c_i$ and a second medical concept $c_j$. The $c_i$ may be a medical concept contained in a patient profile and the $c_j$ may be a medical concept contained in a medical study. The output of the $Sim(c_i, c_j)$ function may be based on the contents of the database 340. The output of the $Sim(c_i, c_j)$ function may be a measure of closeness between the first medical concept $c_i$ and a second medical concept $c_j$. The output of the $Sim(c_i, c_j)$ may be based on a type of relationship (if any) that exists between the first medical concept $c_i$ and a second medical concept $c_j$. The q may be a number of medical concepts in the patient profile minus one. The d may be a number of medical concepts in the medical study minus one.

The database 340 may include information linking different medical concepts. The database 340 may include information regarding relationships between concepts. The database 340 may include information regarding a closeness of a relationship between concepts. The database 340 may include information regarding a type of relationship between two medical concepts. The closeness of the relationship between two medical concepts may be based on the type of relationship that connects the two medical concepts. Medical concepts that are identical may have a closest possible relationship. Medical concepts that are subclasses of each other may be closely related. Medical concepts that have a causal relationship may be related. Medical concepts that frequently appear together may be related. Medical concepts that may have a causal relationship may be weakly related. Medical concepts may be unrelated. The set of discrete medical concepts may be medical concepts contained in the UMLS. The database 340 may include information from the UMLS.

UMLS may include a comprehensive list of biomedical terms. UMLS may be utilized to develop computer systems capable of understanding the specialized vocabulary used in biomedicine and health care. UMLS may include concepts and relationships between concepts. UMLS may unify vocabularies used in different fields of biology and medicine. Concepts listed in multiple vocabularies may be brought together. UMLS may assign a unique identifier to each concept. For example, the concept of fever may hold the UMLS concept unique identifier of C0015967. The concept of fever may be represented in many component vocabularies and have a different identifier or code in each of those vocabularies. Each of the individual codes may represent the same concept. All the codes may be unified into a single biomedical concept in UMLS. The UMLS has been used to facilitate linking health information, medical terms, drug names, and billing codes to create or enhance applications, such as electronic health records, patient classification tools, clinical dictionaries, and medical language translators.

UMLS may include a metathesaurus, a semantic network, and a specialist lexicon. The metathesaurus may include a collection of terms, concepts, and codes from various controlled vocabularies, including PT, ICD-10-CM, LOINC, MeSH, RxNorm, and SNOMED CT. The metathesaurus may include information regarding relationships between and among the concepts and terms. The metathesaurus may describe hierarchies, definitions, and other relationships and attributes. The metathesaurus may be organized by concept, and each concept may have specific attributes defining its meaning. Each concept may be linked to corresponding concept names in the various source vocabularies. The metathesaurus may represent numerous relationships between concepts. The relationship may be a hierarchical one, such as "is-a" for subclasses and "is part of" for subunits. The relationship may be an associative one, such as "is caused by" or "in the literature often occurs close to."

The semantic network may include categories that information from the metathesaurus is divided into. The semantic network may include broad categories (semantic types) and their relationships (semantic relations). The major semantic types may be organisms, anatomical structures, biologic function, chemicals, events, physical objects, and concepts or ideas. The links among semantic types may define the structure of the network and show important relationships between the groupings and concepts. The primary link between semantic types may be the "is-a" link, establishing a hierarchy of types. The semantic network may include categories of non-hierarchical (or associative) relationships, including "physically related to," "spatially related to," "temporally related to," "functionally related to," and "conceptually related to." The information about a semantic type may include an identifier, definition, examples, hierarchical information about the encompassing semantic type(s), and associative relationships. Associative relationships within the semantic network may be weak. An example of an associative relationship may be "may-cause." Applying that associated relationship to the terms smoking and lung cancer would yield: smoking "may-cause" lung cancer.

The specialist lexicon may include a database of lexicographic information for use in natural language processing. The database may include criteria for categorizing concepts in the metathesaurus. The specialist lexicon may define the categories of the semantic network. The specialist lexicon may include tools for normalizing strings, generating lexical variants, and creating indexes. Each entry in the specialist lexicon may include syntactic information (how words are put together to create meaning), morphological information (form and structure) and orthographic information (spelling).

Figure 4:
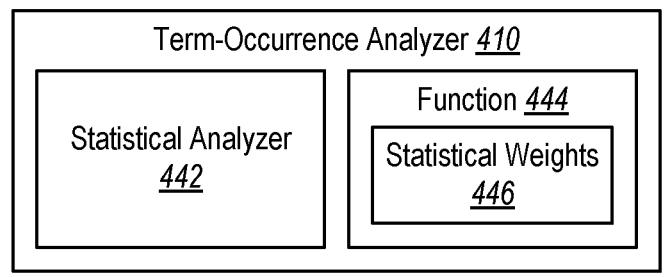
FIG. 4 illustrates an example term-occurrence analyzer for determining a term-occurrence score for a medical study and a patient profile.
Figure 4:
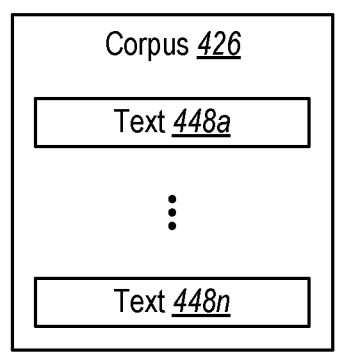

FIG. 4 illustrates an example term-occurrence analyzer 410. The term-occurrence analyzer 410 may include a statistical analyzer 442 and a function 444.

The term-occurrence analyzer 410 may output a term-occurrence score based on an input patient profile and an input medical study. The term-occurrence score may be based on whether terms that appear in the input patient profile (which may be referred to as patient profile terms) also appear in the input medical study. Patient profile terms that also appear in the input medical study may be referred to as overlapping terms. The term-occurrence score may be based on a number of times the overlapping terms appear in the input medical study. The term-occurrence score may be based on a statistical significance of the overlapping terms.

The term-occurrence analyzer 410 may have access to a corpus 426. The corpus 426 may include texts 448a-n. The texts 448a-n may include medical studies and patient profiles.

The statistical analyzer 442 may perform a statistical analysis of the texts 448a-n in the corpus 426. The statistical analysis of the corpus 426 may include determining statistical weights 446. The statistical weights 446 may include a statistical significance of terms included in the texts 448a-n. The statistical significance may be a measure of how informative a term is in distinguishing one document from another document. The statistical significance may be a measure of how important a term is. The statistical significance may be an inverse document frequency. The inverse document frequency may be a measure of how much information a word provides. The inverse document frequency may reflect whether a word is common or rare across all documents. It may be a logarithmically scaled inverse fraction of the documents that contain the word.

The function 444 may output a term-occurrence score based on an input patient profile, an input medical study, a number of occurrences of overlapping terms in the input medical study, and the statistical weights 446 of the overlapping terms in the input medical study. The function 444 may determine a sub term-occurrence score for each of the overlapping terms. The sub term-occurrence score may be based on a number of occurrences of a single overlapping term in the input medical study and a statistical weight of the single overlapping term. The term-occurrence score may be based on the sub term-occurrence scores. For example, the term-occurrence score may be a sum of the sub-term occurrence scores.

The function 444 may include determining one or more term frequency-inverse document frequencies (tf-idf or TFIDF). A TFIDF may be a numerical statistic intended to reflect how important a word is to a document in a collection or corpus. A TFIDF may be used as a weighting factor in searches of information retrieval, text mining, and user modeling. The TFIDF value may increase proportionally to the number of times a word appears in the document and be offset by the number of documents in the corpus that contain the word, which may help adjust for the fact that some words appear more frequently in general.

A TFIDF may be any formula that aims to define the importance of a keyword or phrase within a document. A TFIDF may be a product of two statistics: term frequency and inverse document frequency. The term frequency may be a measure of whether a term occurs in a text or a measure of a frequency of a term in a text. The term frequency may be a relative frequency of a term in a document. The inverse document frequency may be a measure of how much information a word provides. The inverse document frequency may reflect whether a word is common or rare across all documents. It may be a logarithmically scaled inverse fraction of the documents that contain the word.

The function 444 may be a BM25. The BM25 may be based on probabilistic retrieval framework. The BM25 may be a bag-of-words retrieval function that ranks a set of documents based on query terms appearing in each document, regardless of their proximity within the document. One example of a BM25 function may be as follows. Given a query Q, containing keywords $q_1, \ldots, q_n$, the BM25 score of a document D is:

$$\text{score}(D, Q) = \sum_{i=1}^{n} IDF(q_i) \cdot \frac{f(q_i, D) \cdot (k_1 + 1)}{f(q_i, D) + k_1 \cdot \left(1 - b + b \cdot \frac{|D|}{avgdl}\right)}$$

where $f(q_i, D)$ is $q_i$'s term frequency in the document D, $|D|$ is the length of the document D in words, and avgdl is the average document length in the text collection from which documents are drawn. $k_1$ and b are free parameters, usually chosen, in absence of an advanced optimization, as $k_1 \in [1.2, 2.0]$ and $b = 0.75$. $IDF(q_i)$ is the IDF (inverse document frequency) weight of the query term $q_i$. It may be computed as:

$$IDF(q_i) = \ln\left(\frac{N - n(q_i) + 0.5}{n(q_i) + 0.5} + 1\right)$$

where N is the total number of documents in the collection, and $n(q_i)$ is the number of documents containing $q_i$.

In the above example formulas, the document D may be a medical study and the query Q may be a patient profile.

Figure 5:
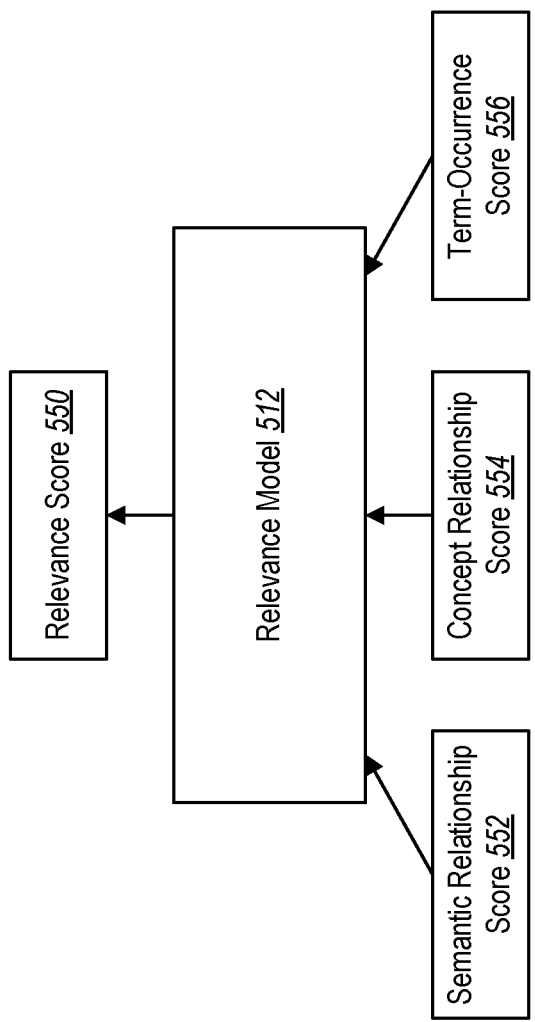
FIG. 5 illustrates an example relevance model for determining a probability that a medical study is relevant to a patient profile.

FIG. 5 illustrates an example relevance model 512.

The relevance model 512 may receive a semantic relationship score 552, a concept relationship score 554, and a term-occurrence score 556 and output a relevance score 550. The relevance score 550 may be a measure of the likelihood that a medical study (such as the medical study 124) is relevant to a patient profile (such as the patient profile 122). A medical study may be relevant to a patient profile if the medical study suits the patient profile's conditions. The semantic relationship score 552, the concept relationship score 554, and the term occurrence score 556 may be based on the medical study and the patient profile. The semantic relationship score 552 may measure a semantic similarity of the patient profile and the medical study. A semantic analyzer (such as the semantic analyzer 102 or the semantic analyzer 202) may output the semantic relationship score 552. The concept relationship score 554 may measure a similarity of medical concepts contained in the patient profile and medical concepts contained in the medical study. A concept relationship analyzer (such as the concept relationship analyzer 108 or the concept relationship analyzer 308) may output the concept relationship score 554. The term-occurrence score 556 may measure a significance of terms that appear in both the patient profile and the medical study. A term-occurrence analyzer (such as the term-occurrence analyzer 110 or the term-occurrence analyzer 410) may output the term-occurrence score 556.

The relevance model 512 may include a deep neural network (DNN). A DNN may be an artificial neural network (ANN) with multiple layers between the input and output layers. A DNN may model complex, non-linear relationships. DNN architectures may generate compositional models where the object is expressed as a layered composition of primitives. The extra layers enable composition of features from lower layers, potentially modeling complex data with fewer units than a similarly performing shallow network. A DNN may be a feedforward network in which data flows from the input layer to the output layer without looping back. At first, a DNN may create a map of virtual neurons and assign random numerical values, or "weights," to connections between them. The weights and inputs may be multiplied and return an output between 0 and 1. An algorithm may adjust the weights and make certain parameters more influential until it determines the correct mathematical manipulation to fully process the data.

The relevance model 512 may be trained to output the relevance score 550. The relevance model 512 may be trained on sets of example semantic relationship scores, example concept relationship scores, and example term-occurrence scores for example patient profiles and example medical studies. The sets of example semantic relationship scores, example concept relationship scores, and example term-occurrence scores may have associated relevance labels. Each relevance label may indicate whether an example medical study is relevant to an example patient profile. The example semantic relationship scores, example concept relationship scores, and example term-occurrence scores may be determined for the example patient profiles and example medical studies by a semantic relationship model, a concept relationship analyzer, and a term-occurrence analyzer.

Figure 6:
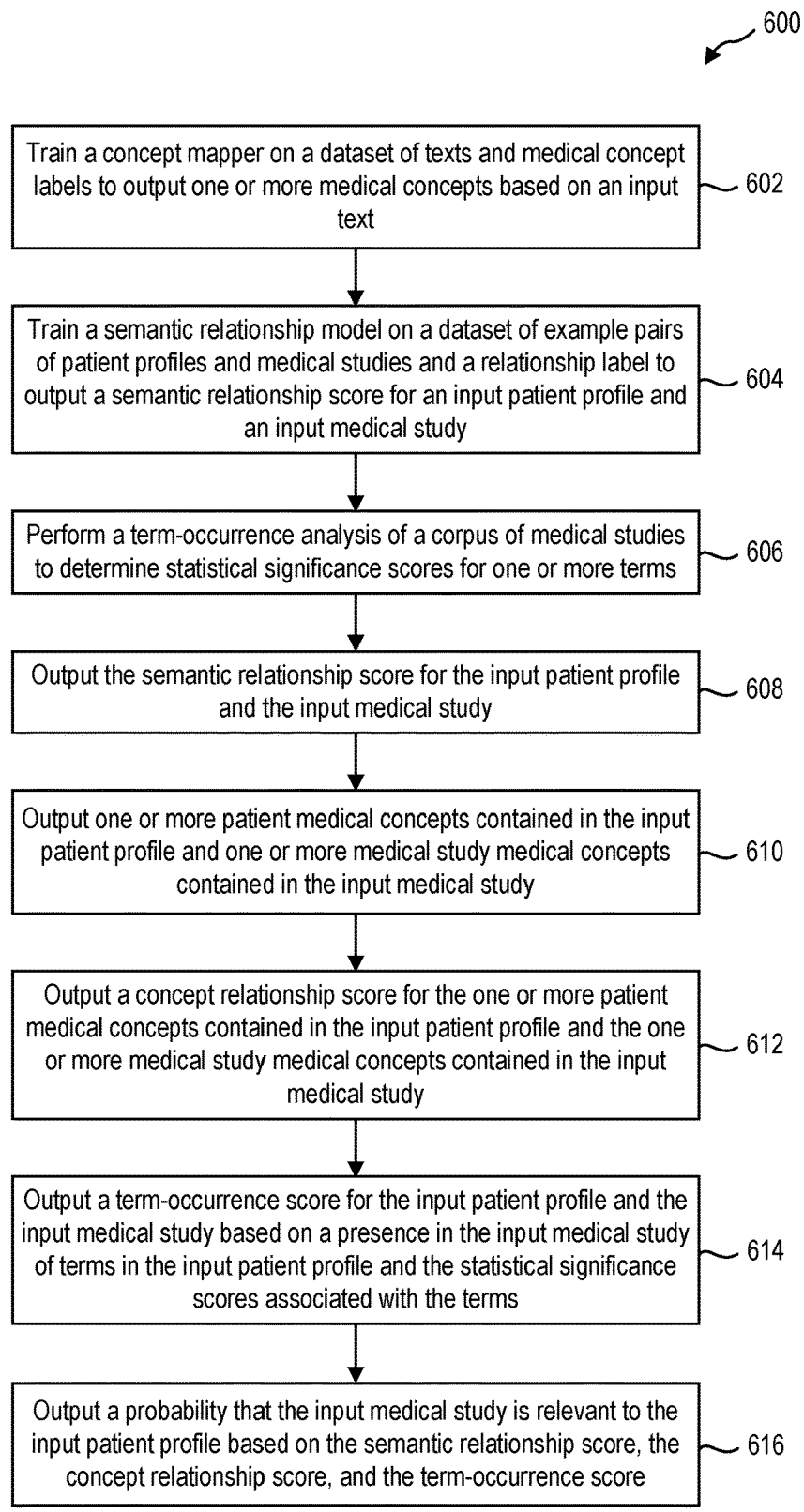
FIG. 6 illustrates an example method for outputting a probability that a medical study is relevant to a patient profile.

FIG. 6 illustrates an example method 600 for determining a probability that a medical study is relevant to a patient profile.

The method 600 may include training 602 a concept mapper on a dataset of texts and medical concept labels to output one or more medical concepts based on an input text. The concept mapper may be the concept mapper 106 or the concept mapper 206.

The method 600 may include training 604 a semantic relationship model on a dataset of example pairs of patient profiles and medical studies and a relationship label to output a semantic relationship score for an input patient profile and an input medical study. The semantic relationship model may be the semantic relationship model 104 or the semantic relationship model 204. Training 604 the semantic relationship model on the data set of example pairs of patient profiles and medical studies and a relationship label may include training the semantic relationship model on the data set of example pairs of patient profiles and medical studies, the relationship label, and medical concepts contained in the example pairs of patient profiles and medical studies.

The method 600 may include performing 606 a term-occurrence analysis of a corpus of medical studies to determine statistical significance scores for one or more terms. The term-occurrence analyzer 110 or the term-occurrence analyzer 410 may perform the term-occurrence analysis. The statistical significance scores may be the statistical weights 446.

The method 600 may include outputting 608 the semantic relationship score for the input patient profile and the input medical study. The semantic relationship model may output the semantic relationship score. The semantic relationship score may be the semantic relationship score 552.

The method 600 may include outputting 610 one or more patient medical concepts contained in the input patient profile and one or more medical study medical concepts contained in the input medical study. The concept mapper 106 or the concept mapper 206 may output the one or more patient medical concepts and the one or more medical study medical concepts.

The method 600 may include outputting 612 a concept relationship score for the one or more patient medical concepts contained in the input patient profile and the one or more medical study medical concepts contained in the input medical study. The concept relationship analyzer 108 or the concept relationship analyzer 308 may output the concept relationship score. The concept relationship score may be the concept relationship score 554.

The method 600 may include outputting 614 a term-occurrence score for the input patient profile and the input medical study based on a presence in the input medical study of terms in the input patient profile and the statistical significance scores associated with the terms. The term-occurrence analyzer 110 or the term-occurrence analyzer 410 may output the term-occurrence score. The term occurrence score may be the term-occurrence score 556.

The method 600 may include outputting 616 a probability that the input medical study is relevant to the input patient profile based on the semantic relationship score, the concept relationship score, and the term-occurrence score. The relevance model 112 or the relevance model 512 may output the probability. The probability may be the relevance score 550.

Figure 7:
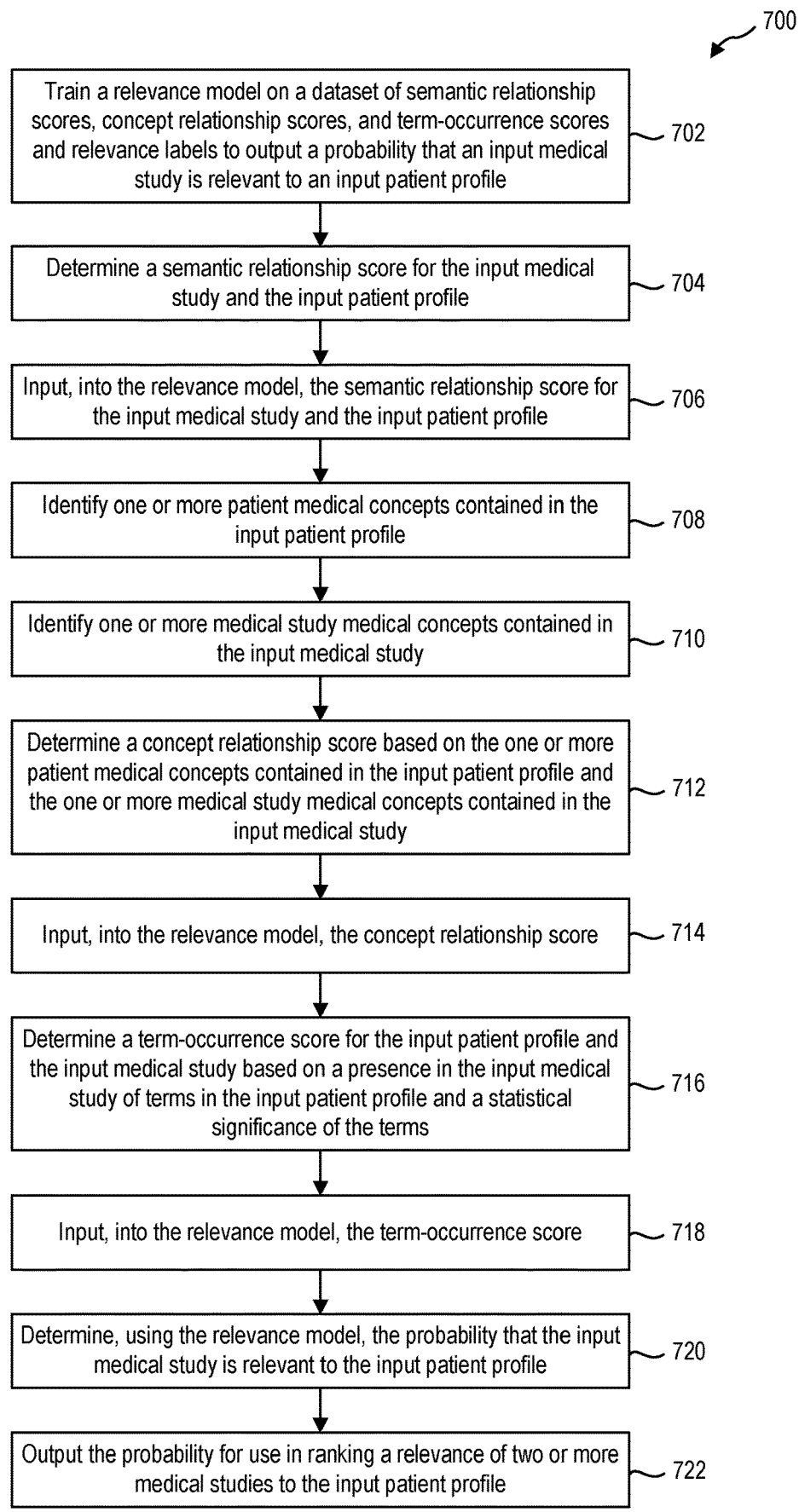
FIG. 7 illustrates an example method for ranking medical studies based on probability of relevance to a patient profile.

FIG. 7 illustrates an example method 700 for ranking a relevance of medical studies to a patient profile.

The method 700 may include training 702 a relevance model on a dataset of semantic relationship scores, concept relationship scores, and term-occurrence scores and relevance labels to output a probability that an input medical study is relevant to an input patient profile. The relevance model may be the relevance model 112 or the relevance model 512. The semantic relationship scores may be determined by a semantic relationship model. The concept relationship scores may be determined by a concept relationship analyzer. The term-occurrence scores may be determined by a term-occurrence analyzer.

The method 700 may include determining 704 a semantic relationship score for the input medical study and the input patient profile. A semantic relationship model (such as the semantic relationship model 104 or the semantic relationship model 204) may determine the semantic relationship score for the input medical study and the input patient profile. The semantic relationship score may be the semantic relationship score 552.

The method 700 may include inputting 706, into the relevance model, the semantic relationship score for the input medical study and the input patient profile.

The method 700 may include identifying 708 one or more patient medical concepts contained in the input patient profile. A concept mapper (such as the concept mapper 106 or the concept mapper 206) may identify the one or more patient medical concepts contained in the input patient profile.

The method 700 may include identifying 710 one or more medical study medical concepts contained in the input medical study. A concept mapper (such as the concept mapper 106 or the concept mapper 206) may identify the one or more medical study medical concepts contained in the input medical study.

The method 700 may include determining 712 a concept relationship score based on the one or more patient medical concepts contained in the input patient profile and the one or more medical study medical concepts contained in the input medical study. A concept relationship analyzer (such as the concept relationship analyzer 108 or the concept relationship analyzer 308) may determine the concept relationship score. The concept relationship score may be the concept relationship score 554.

The method 700 may include inputting 714, into the relevance model, the concept relationship score.

The method 700 may include determining 716 a term-occurrence score for the input patient profile and the input medical study based on a presence in the input medical study of terms in the input patient profile and a statistical significance of the terms. A term-occurrence analyzer (such as the term-occurrence analyzer 110 or the term-occurrence analyzer 410) may determine the term-occurrence score. The term-occurrence score may be the term-occurrence score 556.

The method 700 may include inputting 718, into the relevance model, the term-occurrence score.

The method 700 may include determining 720, using the relevance model, the probability that the input medical study is relevant to the input patient profile. The probability may be the relevance score 550.

The method 700 may include outputting 722 the probability for use in ranking a relevance of two or more medical studies to the input patient profile. A ranking module (such as the ranking module 114) may rank the relevance of the two or more medical studies to the input patient profile.

Figure 8:
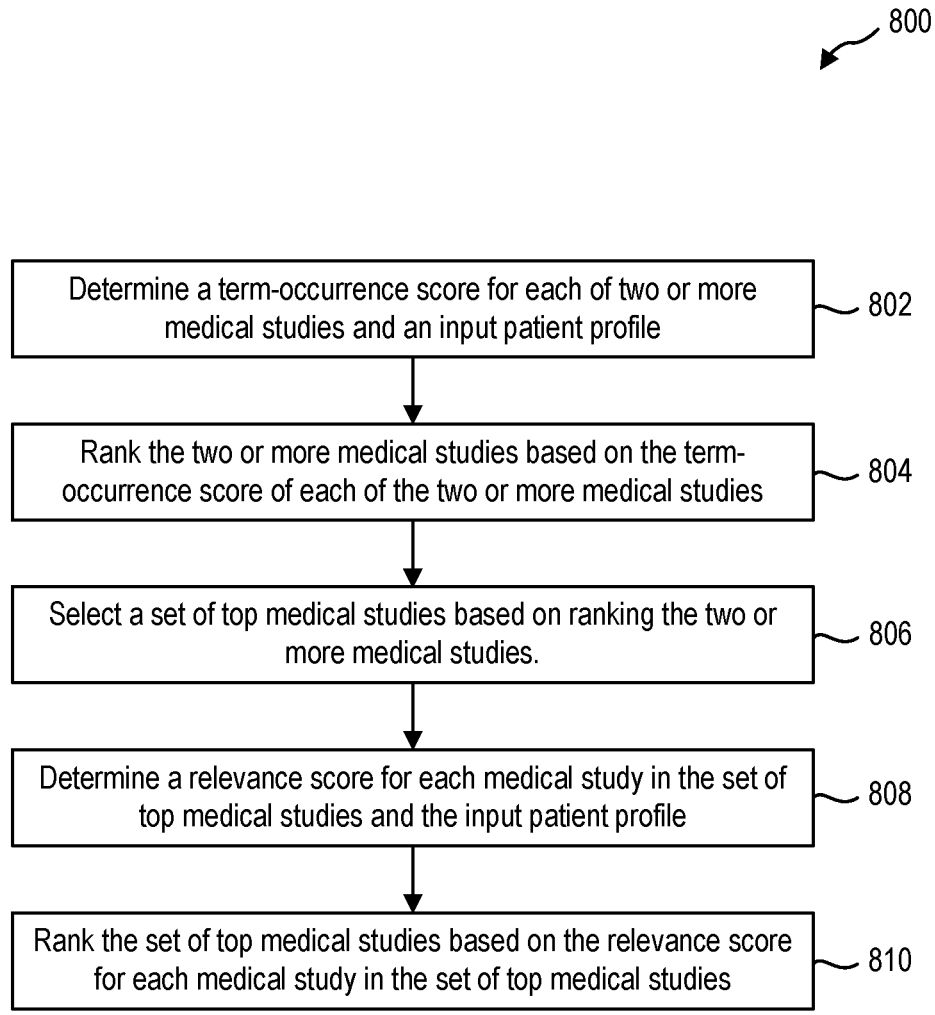
FIG. 8 illustrates an example for selecting a set of top medical studies and ranking medical studies within the set of top medical studies.

FIG. 8 illustrates an example method 800 for ranking a relevance of medical studies to a patient profile.

The method 800 may include determining 802 a term-occurrence score for each of two or more medical studies and an input patient profile.

The method 800 may include ranking 804 the two or more medical studies based on the term-occurrence score of each of the two or more medical studies.

The method 800 may include selecting 806 a set of top medical studies based on ranking the two or more medical studies. The set of top medical studies may be medical studies within the two or more medical studies that received a term-occurrence score greater than a threshold. The set of top medical studies may be a certain percentage of the two or more medical studies that have the highest term-occurrence scores. The set of top medical studies may be a certain number of the two or more medical studies that have the highest term-occurrence scores.

The method 800 may include determining 808 a relevance score for each medical study in the set of top medical studies and the input patient profile.

The method 800 may include ranking 810 the set of top medical studies based on the relevance score for each medical study in the set of top medical studies.

Figure 9:
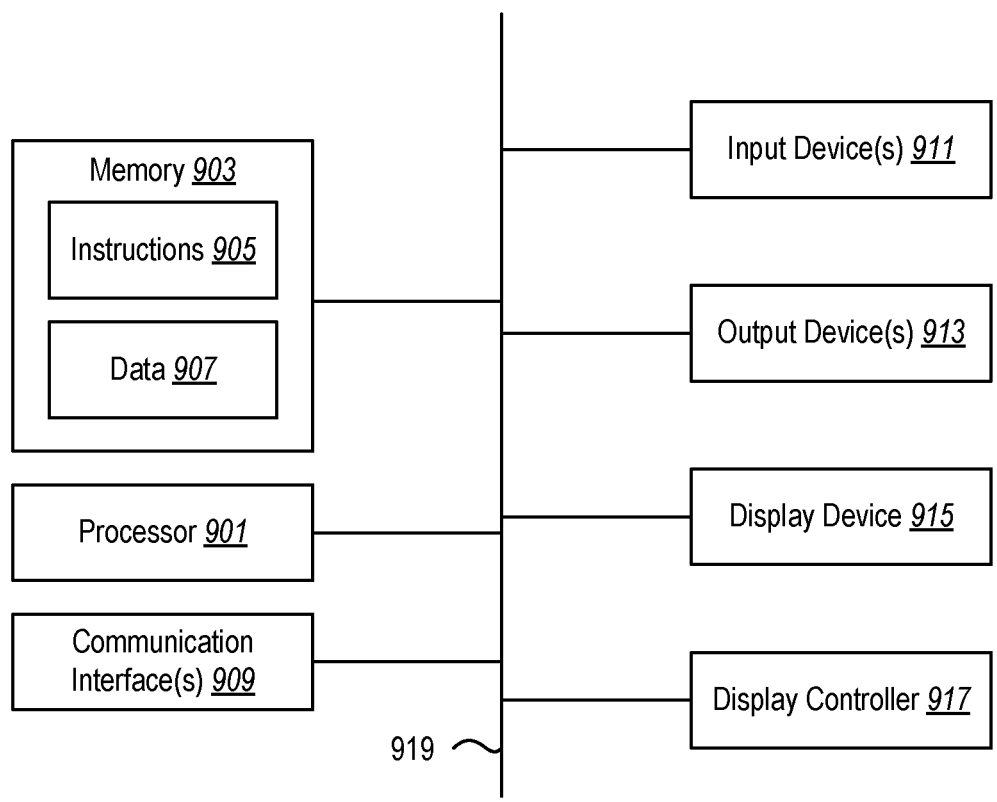
FIG. 9 illustrates certain components that can be included within a computing device.

Reference is now made to FIG. 9. One or more computing devices 900 can be used to implement at least some aspects of the techniques disclosed herein. FIG. 9 illustrates certain components that can be included within a computing device 900.

The computing device 900 includes a processor 901 and memory 903 in electronic communication with the processor 901. Instructions 905 and data 907 can be stored in the memory 903. The instructions 905 can be executable by the processor 901 to implement some or all of the methods, steps, operations, actions, or other functionality that is disclosed herein. Executing the instructions 905 can involve the use of the data 907 that is stored in the memory 903. Unless otherwise specified, any of the various examples of modules and components described herein can be implemented, partially or wholly, as instructions 905 stored in memory 903 and executed by the processor 901. Any of the various examples of data described herein can be among the data 907 that is stored in memory 903 and used during execution of the instructions 905 by the processor 901.

Although just a single processor 901 is shown in the computing device 900 of FIG. 9, in an alternative configuration, a combination of processors (e.g., an Advanced RISC (Reduced Instruction Set Computer) Machine (ARM) and a digital signal processor (DSP)) could be used.

The computing device 900 can also include one or more communication interfaces 909 for communicating with other electronic devices. The communication interface(s)

909 can be based on wired communication technology, wireless communication technology, or both. Some examples of communication interfaces 909 include a Universal Serial Bus (USB), an Ethernet adapter, a wireless adapter that operates in accordance with an Institute of Electrical and Electronics Engineers (IEEE) 802.11 wireless communication protocol, a Bluetooth® wireless communication adapter, and an infrared (IR) communication port.

The computing device 900 can also include one or more input devices 911 and one or more output devices 913. Some examples of input devices 911 include a keyboard, mouse, microphone, remote control device, button, joystick, trackball, touchpad, and lightpen. One specific type of output device 913 that is typically included in a computing device 900 is a display device 915. Display devices 915 used with embodiments disclosed herein can utilize any suitable image projection technology, such as liquid crystal display (LCD), light-emitting diode (LED), gas plasma, electroluminescence, wearable display, or the like. A display controller 917 can also be provided, for converting data 907 stored in the memory 903 into text, graphics, and/or moving images (as appropriate) shown on the display device 915. The computing device 900 can also include other types of output devices 913, such as a speaker, a printer, etc.

The various components of the computing device 900 can be coupled together by one or more buses, which can include a power bus, a control signal bus, a status signal bus, a data bus, etc. For the sake of clarity, the various buses are illustrated in FIG. 9 as a bus system 919.

The techniques disclosed herein can be implemented in hardware, software, firmware, or any combination thereof, unless specifically described as being implemented in a specific manner. Any features described as modules, components, or the like can also be implemented together in an integrated logic device or separately as discrete but interoperable logic devices. If implemented in software, the techniques can be realized at least in part by a non-transitory computer-readable medium having computer-executable instructions stored thereon that, when executed by at least one processor, perform some or all of the steps, operations, actions, or other functionality disclosed herein. The instructions can be organized into routines, programs, objects, components, data structures, etc., which can perform particular tasks and/or implement particular data types, and which can be combined or distributed as desired in various embodiments.

The term "processor" can refer to a general purpose single- or multi-chip microprocessor (e.g., an Advanced RISC (Reduced Instruction Set Computer) Machine (ARM)), a special purpose microprocessor (e.g., a digital signal processor (DSP)), a microcontroller, a programmable gate array, or the like. A processor can be a central processing unit (CPU). In some embodiments, a combination of processors (e.g., an ARM and DSP) could be used to implement some or all of the techniques disclosed herein.

The term "memory" can refer to any electronic component capable of storing electronic information. For example, memory may be embodied as random access memory (RAM), read-only memory (ROM), magnetic disk storage media, optical storage media, flash memory devices in RAM, various types of storage class memory, on-board memory included with a processor, erasable programmable read-only memory (EPROM), electrically erasable programmable read-only memory (EEPROM) memory, registers, and so forth, including combinations thereof.

The steps, operations, and/or actions of the methods described herein may be interchanged with one another without departing from the scope of the claims. In other words, unless a specific order of steps, operations, and/or actions is required for proper functioning of the method that is being described, the order and/or use of specific steps, operations, and/or actions may be modified without departing from the scope of the claims.

The term "determining" (and grammatical variants thereof) can encompass a wide variety of actions. For example, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The terms "comprising," "including," and "having" are intended to be inclusive and mean that there can be additional elements other than the listed elements. Additionally, it should be understood that references to "one embodiment" or "an embodiment" of the present disclosure are not intended to be interpreted as excluding the existence of additional embodiments that also incorporate the recited features. For example, any element or feature described in relation to an embodiment herein may be combinable with any element or feature of any other embodiment described herein, where compatible.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A system for determining a relevance of an input medical study to an input patient profile, the system comprising:
    one or more processors;
    memory in electronic communication with the one or more processors; and
    instructions stored in the memory, the instructions being executable by the one or more processors to:
        identify overlapping terms for the input patient profile and the input medical study, wherein the overlapping terms are terms contained in the input patient profile that also appear in the input medical study;
        determine a term-occurrence score for the input medical study and the input patient profile, wherein the term-occurrence score is based on a number of occurrences of the overlapping terms in the input medical study and statistical weights associated with the overlapping terms;
        map sets of text in the input medical study to a first set of medical concepts;
        map sets of text in the input patient profile to a second set of medical concepts, wherein the second set of medical concepts is separate from the first set of medical concepts;
        determine a concept relationship score for the input medical study and the input patient profile, wherein the concept relationship score measures a closeness of relationship between the first set of medical concepts and the second set of medical concepts;
        determine a semantic relationship score for the input medical study and the input patient profile based on a first semantic meaning of text contained in the input medical study and a second semantic meaning of text contained in the input patient profile; and determine a probability that the input medical study is relevant to the input patient profile based on the term-occurrence score, the concept relationship score, and the semantic relationship score.

2. The system of claim 1, wherein determining the semantic relationship score for the input medical study and the input patient profile is further based on the first set of medical concepts and the second set of medical concepts.

3. The system of claim 2 further comprising:
determining the first semantic meaning of text contained in the input medical study and the second semantic meaning of text contained in the input patient profile based on deep contextual representation.

4. The system of claim 3, wherein determining the first semantic meaning of text contained in the input medical study and the second semantic meaning of text contained in the input patient profile based on deep contextual representation is based on a BERT (bidirectional encoder representations from transformers) model or an ELMo (embeddings from language models) model.

5. The system of claim 1, wherein the statistical weights associated with the overlapping terms are based on a statistical analysis of a corpus of medical studies.

6. The system of claim 5, wherein determining the term-occurrence score is further based on determining a sub term-occurrence score based on a number of appearances of a single overlapping term in the input medical study and a statistical weight of the single overlapping term.

7. The system of claim 1, wherein determining the concept relationship score for the first set of medical concepts and the second set of medical concepts is based on a knowledge graph of medical concepts, wherein the knowledge graph comprises links among the medical concepts and the knowledge graph comprises the first set of medical concepts and the second set of medical concepts.

8. The system of claim 7, wherein medical concepts in the first set of medical concepts and the second set of medical concepts are contained in a Unified Medical Language System (UMLS).

9. The system of claim 1 further comprising:
ranking the input medical study against one or more other medical studies based on the probability that the input medical study is relevant to the input patient profile and probabilities that the one or more other medical studies are relevant to the input patient profile.

10. The system of claim 9 further comprising:
selecting the one or more other medical studies from a set of medical studies based on term-occurrence scores for each medical study in the set of medical studies and the input patient profile.

11. A method for determining semantic similarity between an input medical study and an input patient profile, the method comprising:
receiving the input medical study and the input patient profile;
mapping sets of text in the input medical study to a first set of medical concepts;
mapping sets of text in the input patient profile to a second set of medical concepts, wherein the second set of medical concepts is separate from the first set of medical concepts;
determining a first semantic meaning of text in the input patient profile;
determining a second semantic meaning of text in the input medical study; and
determining a semantic similarity score for the input patient profile and the input medical study based on the first set of medical concepts, the second set of medical concepts, the first semantic meaning, and the second semantic meaning.

12. The method of claim 11, wherein determining the first semantic meaning and the second semantic meaning is based on deep contextual representation.

13. The method of claim 12, wherein determining the first semantic meaning and the second semantic meaning based on deep contextual representation is based on a BERT (bidirectional encoder representations from transformers) model or an ELMo (embeddings from language models) model.

14. A computer-readable medium comprising instructions that are executable by one or more processors to cause a computing system to:
receive a medical study and a patient profile;
identify overlapping terms for the patient profile and the medical study, wherein the overlapping terms are terms contained in the patient profile that also appear in the medical study;
determine a term-occurrence score for the medical study and the patient profile, wherein the term-occurrence score is based on a number of occurrences of the overlapping terms in the medical study and statistical weights associated with the overlapping terms;
map sets of text in the medical study to a first set of medical concepts;
map sets of text in the patient profile to a second set of medical concepts, wherein the second set of medical concepts is separate from the first set of medical concepts;
determine a concept relationship score for the patient profile and the medical study, wherein the concept relationship score measures a closeness of relationship between the first set of medical concepts and the second set of medical concepts;
determine a semantic relationship score for the medical study and the patient profile based on comparing a first semantic meaning of text contained in the medical study and a second semantic meaning of text contained in the patient profile and based on the first set of medical concepts and the second set of medical concepts; and
determine a probability that the medical study is relevant to the patient profile based on the term-occurrence score, the concept relationship score, and the semantic relationship score.

15. The computer-readable medium of claim 14, wherein the statistical weights associated with the overlapping terms are based on a statistical analysis of a corpus of medical studies.

16. The computer-readable medium of claim 15, wherein determining the term-occurrence score is further based on determining a sub term-occurrence score based on a number of appearances of a single overlapping term in the medical study and a statistical weight of the single overlapping term.

17. The computer-readable medium of claim 14, wherein determining the concept relationship score for the first set of medical concepts and the second set of medical concepts is based on a knowledge graph of medical concepts, wherein the knowledge graph comprises links among the medical concepts and the knowledge graph comprises the first set of medical concepts and the second set of medical concepts.

18. The computer-readable medium of claim 17, wherein medical concepts in the first set of medical concepts and the second set of medical concepts are contained in a Unified Medical Language System (UMLS).

19. The computer-readable medium of claim 14 further comprising instructions that are executable by the one or more processors to cause the computing system to:
rank the medical study against one or more other medical studies based on the probability that the medical study is relevant to the patient profile and probabilities that the one or more other medical studies are relevant to the patient profile.

20. The computer-readable medium of claim 19 further comprising instructions that are executable by the one or more processors to cause the computing system to:
select the one or more other medical studies from a set of medical studies based on term-occurrence scores for each medical study in the set of medical studies and the patient profile.

\* \* \* \* \*